United States Patent
Reeve et al.

(10) Patent No.: US 12,005,423 B2
(45) Date of Patent: Jun. 11, 2024

(54) MODIFIED POLYAMINES GRAFTED TO A PARTICULATE, SOLID SUPPORT AS SORBENT MATERIALS FOR REMOVAL OF TARGET SUBSTANCES FROM FLUIDS

(71) Applicant: Puraffinity Ltd., London (GB)

(72) Inventors: Benjamin David Reeve, London (GB); Wen Li, London (GB); Katharina Reeh, London (GB); Amanda Yi Fen You, London (GB); Henrik Hagemann, London (GB)

(73) Assignee: Puraffinity Ltd., London (GB)

( * ) Notice: Subject to any disclaimer, the term of this patent is extended or adjusted under 35 U.S.C. 154(b) by 704 days.

(21) Appl. No.: 17/041,531

(22) PCT Filed: Mar. 28, 2019

(86) PCT No.: PCT/GB2019/050886
§ 371 (c)(1),
(2) Date: Sep. 25, 2020

(87) PCT Pub. No.: WO2019/186166
PCT Pub. Date: Oct. 3, 2019

(65) Prior Publication Data
US 2021/0008522 A1    Jan. 14, 2021

(30) Foreign Application Priority Data
Mar. 28, 2018  (GB) ...................................... 1805058

(51) Int. Cl.
*B01J 20/26*    (2006.01)
*B01D 69/14*    (2006.01)
(Continued)

(52) U.S. Cl.
CPC .......... *B01J 20/267* (2013.01); *B01D 69/147* (2013.01); *B01J 20/103* (2013.01); *B01J 20/24* (2013.01);
(Continued)

(58) Field of Classification Search
CPC . B01J 20/10; B01J 20/103; B01J 20/24; B01J 20/262; B01J 20/267;
(Continued)

(56) References Cited

U.S. PATENT DOCUMENTS 10,836,654 B1    11/2020  Gray et al.
2011/0147292 A1  6/2011   Demmer et al.
(Continued)

FOREIGN PATENT DOCUMENTS

CN    1053046      * 7/1991 ............. B01D 69/02
JP    2013078724 A    5/2013
(Continued)

OTHER PUBLICATIONS

Machine translation of CN1053046. (Year: 1991).*

*Primary Examiner* — Brian A McCaig
(74) *Attorney, Agent, or Firm* — NIXON PEABODY LLP; David S. Resnick; Nicole D. Kling

(57) ABSTRACT

Provided are compositions for removal of a target substance from a fluid stream, the composition comprising a polyamine; and a covalently linked hydrophobic group, wherein the polyamine is covalently linked to a support material. Also provided are processes for removal of a target substance from a fluid stream comprising contacting the fluid stream with a composition comprising a polyamine; and a covalently linked hydrophobic group, wherein the polyamine is covalently linked to a support material.

25 Claims, 3 Drawing Sheets

(51) Int. Cl.
 *B01J 20/10* (2006.01)
 *B01J 20/24* (2006.01)
 *B01J 20/28* (2006.01)
 *B01J 20/32* (2006.01)
 *C02F 1/28* (2023.01)
 *C02F 1/44* (2023.01)
 *C07C 53/21* (2006.01)
 *C07C 309/65* (2006.01)
 *C22B 3/24* (2006.01)
 *C22B 11/00* (2006.01)
 *C22B 59/00* (2006.01)
 *C02F 101/36* (2006.01)

(52) U.S. Cl.
 CPC ... *B01J 20/28004* (2013.01); *B01J 20/28016* (2013.01); *B01J 20/28038* (2013.01); *B01J 20/3204* (2013.01); *B01J 20/3212* (2013.01); *B01J 20/3219* (2013.01); *B01J 20/3278* (2013.01); *C02F 1/285* (2013.01); *C02F 1/288* (2013.01); *C02F 1/44* (2013.01); *C07C 53/21* (2013.01); *C07C 309/65* (2013.01); *C22B 3/24* (2013.01); *C22B 11/04* (2013.01); *C22B 59/00* (2013.01); *C02F 2101/36* (2013.01)

(58) Field of Classification Search
 CPC ............ B01J 20/28004; B01J 20/28016; B01J 20/28038; B01J 20/3071; B01J 20/3085; B01J 20/3092; B01J 20/3204; B01J 20/3212; B01J 20/3219; B01J 20/3278; B01J 20/245; B01J 2220/4825; B01D 69/17; B01D 71/60; C02F 1/285; C02F 1/288; C02F 1/44; C07C 53/21; C07C 309/65; C22B 3/24; C22B 11/04; C22B 59/00
 See application file for complete search history.

(56) References Cited

U.S. PATENT DOCUMENTS

| | | |
|---|---|---|
| 2014/0202964 A1 | 7/2014 | Gu et al. |
| 2015/0344520 A1 | 12/2015 | Matsumoto et al. |
| 2022/0055015 A1 | 2/2022 | Kupracz |

FOREIGN PATENT DOCUMENTS

| | | |
|---|---|---|
| WO | 2013/050139 A1 | 4/2013 |
| WO | 2017178100 A1 | 10/2017 |

\* cited by examiner

MODIFIED POLYAMINES GRAFTED TO A PARTICULATE, SOLID SUPPORT AS SORBENT MATERIALS FOR REMOVAL OF TARGET SUBSTANCES FROM FLUIDS

CROSS REFERENCE TO RELATED APPLICATIONS

This Application is a 35 U.S.C. § 371 National Phase Entry of International Patent Application No. PCT/GB2019/050886 filed Mar. 28, 2019, which designates the U.S. and claims benefit of foreign priority under 35 U.S.C. § 119(b) of GB Application Number 1805058.3 filed Mar. 28, 2018, the contents of which are incorporated herein in their entireties by reference.

FIELD OF THE INVENTION

The invention is concerned with the removal of target substances from fluids, such as liquids, using chemically modified filtration materials based on polyamines, as well as methods for the production of such materials.

BACKGROUND OF THE INVENTION

Growing industrialisation around the world, combined with increasing demand for cheaply manufactured products, has contributed to a significant and on-going need for the remediation and recycling of contaminated supplies of key solvents, such as water. There is an appreciation that it is necessary to re-use and replenish existing resources rather than simply dispose of them. Environmental protection regulations have also become increasingly stringent as dwindling fresh water supplies have become threatened with contamination from industrial activity.

Important fluids used in industrial and agricultural processes include not only water, but also solvents, fuels, lubricants and working fluids. All of these fluids can be exposed to chemical contamination through normal use in industrial processes, or via exposure to waste products, whether intentionally or accidentally. By way of example, in industrialised countries typically up to two thirds of all water consumption can be attributed to the needs of industry. It is not surprising that at an international level there are significant efforts from organisations such as the United Nations to ensure that developed and developing nations commit to sustainable environmental policies including the responsible use of water. In particular, it is essential that better ways of getting more out of each unit of water consumed are developed to support sustainable growth.

There are diverse sources of environmentally damaging pollutants, including wastewater from industrial plants and chemical process facilities which has been improperly disposed of; surface runoff containing fertilisers and pesticides used on agricultural areas; and cleaning detergents as well as flame retardants used in fire-fighting foams. Many industrial chemical contaminants can persist in nature for many years before degrading, and can cause great harm to plants, animals and humans, even at very low concentrations. The impact on ecological systems is also profound, with persistent pollutants often concentrating in the bodies of organisms higher up the food chain. Despite being banned in most industrial nations in the late 1970s, polychlorinated biphenyls (PCBs) can still be found at high levels in the tissues of many marine animals, causing disruption of normal endocrine processes.

In addition to environmentally damaging pollutants, it is also common for fluids used in industrial, pharmaceutical and agricultural processes to contain economically valuable components or chemicals, such as precious metals including silver or or gold, palladium and platinum group metals (Sharma et al 2017 https://pubs.rsc.org/en/content/articlehtml/2017/ra/c7ra10153h), other metals including lithium, or small molecules including drugs. While in many contexts such chemicals can often be viewed as harmful contaminants in their own right, removal and/or reclamation of these contents can also be valuable in that they can then be reused, rather than lost. For example, water (such as rainwater) passing through refuse from mining operations can contain dissolved minerals which were present at concentrations too low to be worth refining, but which could both pose an environmental hazard, and represent a possible source for increasing production from mining.

Hence, there exists a significant need to provide novel and innovative solutions to the problem of remediation of contaminated fluid streams, especially contaminated water.

One particular class of persistent environmental pollutants includes halogenated organic compounds such as poly- and perfluorinated alkyl substances (PFAS). PFAS are organofluorine compounds. Whilst they are considered to be chemically inert, they are persistent in the environment, and their use is controlled in many countries by the United Nations Framework Convention on Climate, the "Kyoto Protocol". PFAS are also used as precursors for the manufacture of a number of derivative compounds that do represents an environmental risk, including fluorosurfactants, fluoropolymers and organofluorine reactants. Perfluorooctane sulfonate (PFOS) and perfluorooctanoic acid (PFOA) are toxic PFAS compounds that are used extensively as surfactants and in flame retardants for fire-fighting foams and metal plating processes. Both PFOS and PFOA persist in the environment for very long periods of time and are recognised contaminants in most of the world's fresh water supplies.

Adsorption of PFAS compounds such as PFOS and PFOA, onto granular activated carbon represents the current best and recommended solution for their removal from contaminated water. However, the process is very slow and inefficient. In particular, the charged and shorter chain, PFAS pollutants quickly "break-through" beds of activated carbon, meaning very large quantities of activated carbon are required, which must be frequently replaced once saturated with PFAS. Adsorbed PFAS cannot be washed off activated carbon for regeneration "in situ". Hence, the activated carbon represents an expensive and single use solution to the problem of removing PFAS from contaminated water.

Some modified cellulose materials show better removal, but have only been effective at reducing high concentration perfluorinated surfactants to lower levels, not at cleaning them completely from levels at >1 ppm to within regulatory limits (for example set by the United States Environmental Protection Agency around 70 parts per trillion: https://www.epa.gov/ground-water-and-drinking-water/drinking-water-health-advisories-pfoa-and-pfos). Such materials have only been effective as a pre-treatment to extend the life of activated carbon, not as a complete solution to PFC removal. They also act as a dispersed flocculant and require complex and unique equipment for implementation (see for example, EP2763790B1).

Speciality ion exchange resins are also an emerging solution. Here, styrene divinyl benzene polymer beads, modified with quaternary ammonium, are used in packed beds as an alternative to activated carbon. These resins either cannot be regenerated or can only be regenerated with a toxic and flammable solvent (see for example WO2017180346A1).

Hence, there exists a need to provide economical and re-usable compositions and processes that enable the removal of low concentrations (<1 ppm) of target substances, in particular valuable materials, or polluting contaminants, such as PFAS, from fluid streams, such as wastewater. It is apparent that such a goal is especially challenging with current technologies. The present invention seeks to overcome the present challenges and meet these objectives.

SUMMARY OF THE INVENTION

A first aspect of the invention provides a composition for removal of a target substance from a fluid stream, the composition comprising a polyamine; and a covalently linked hydrophobic group, wherein the polyamine is covalently linked to a support material.

The support material may typically be a porous, solid and/or particulate support material. Suitably the support material comprises cellulose, and is comprised of a material selected from one or more of the group consisting of: lignocellulose; microcrystalline cellulose; microfibrillated cellulose; bacterial cellulose; and a cellulose derivative. Optionally, the support material can be a powder or pulp, such as a cellulose or lignocellulose powder or pulp. If in particulate form, the support material can comprise for example one or more of the group consisting of a plurality of: granules; flakes; beads; pellets; and pastilles.

The support material may also be selected from one or more of the group consisting of: silica; silica gel; and a silica derivative.

In an embodiment of the invention, the polyamine is selected from a linear or branched polyamine. Suitably the polyamine is selected from a linear or branched polyamine selected from: polyethylenimine (PEI); polypropylenimine (PPI); poly(allylamine), poly(vinylamine), poly(N-methylvinylamine)polylysine, poly(4-aminostyrene).

In an alternative embodiment of the invention, the polyamine is selected from a cationic polyamine such as poly(diallyldimethylammonium chloride), a guanidine polyamine such as polyhexamethylene guanidine or polyhexanide, or a polyamine copolymer such as poly(acrylamide-co-diallyldimethylammonium chloride) or poly(methylene co-guanidine).

In a further embodiment the hydrophobic group comprises a group selected from: a C2-C22 branched, linear or cyclic, saturated or unsaturated alkyl; or an aryl. Typically, this group is selected from a C2-C22 branched, linear or cyclic alkyl; or an aryl. Optionally the C2-C22 branched or linear alkyl group is selected from a butyl, hexyl or octyl group. Suitably, the C2-C22 linear alkyl group is a C4-C8 branched or linear alkyl selected from an isobutyl, isohexyl or isooctyl group. In a specific embodiment of the invention the C2-C22 alkyl group is a cycloalkyl selected from a cyclohexyl, cycloheptyl or cyclooctyl group. In a further embodiment, the aryl group is selected from the group consisting of: a phenol, benzene or benzyl. In a further embodiment the hydrophobic group is a C2-C22 poly or perfluorinated group, suitably a C8 perfluorooctane or C8 polyfluorinated, 6:2 fluorotelomer. Optionally the sorbent molecule comprises a plurality of hydrophobic groups.

According to specific embodiments of the present invention, the polyamine group is linked to the hydrophobic group via an amide bond. The polyamine and hydrophobic group may alternatively be linked via a urea linkage, a thiourea linkage; an isothiouronium linkage, a guanidinium linkage or directly via an alkylation reaction, or a quaternisation (Menshutkin) reaction.

A second aspect of the invention provides for a process for removal of a target substance from a fluid stream comprising contacting the fluid stream with a composition comprising a polyamine; and a covalently linked hydrophobic group, wherein the polyamine is covalently linked to a support material.

Typically the fluid is a liquid, optionally the liquid is selected from: water; an organic solvent; a liquid fossil fuel; a liquid lubricant; and a working fluid.

In a specific embodiment of the invention, the target substance is a contaminant. The contaminant may comprise one or more poly- and perfluorinated alkyl substance (PFAS), optionally selected from a perfluorinated anionic surfactant compound, including one or more selected from the group consisting of: perfluorooctanoic acid (PFOA); perfluorobutane sulfonate (PFBS); perfluorobutanoic acid (PFBA); perfluorohexanesulfonate (PFHS); perfluorohexanoic acid (PFHA); perfluorooctane sulfonate (PFOS); perfluorononanoic acid (PFNA); and perfluorodecanoic acid (PFDA). Alternatively, the contaminant may comprise an organic compound, optionally a pharmaceutical or pesticide molecule including one or more selected from the group: diclofenac, erythromycin, estrogens, oxadiazon and thiamethoxam.

Alternatively the contaminant may be a metal or metalloid ion optionally selected from copper, iron, lead, mercury, chromate or arsenate.

In another embodiment of the invention, the target substance comprises a valuable substance, optionally comprising gold, silver, rare earth metals or platinum group metals or their salts.

In a specific embodiment the support material is deployed within a bed or a packed column and the fluid stream is passed through or across the bed or packed column.

According to a further embodiment of the invention the process further comprises regenerating the composition after removal of the target substance from the fluid stream. Suitably, the step of regenerating the composition comprises applying an aqueous wash to the sorbent material or a series of washes. Optionally, regeneration of the support material comprises applying a salt wash, or acidic wash or basic wash to the composition. The wash may comprise a liquid having a pH greater than 9, or alternatively a pH of less than 5. In some embodiments, regeneration of the support material comprises applying an aqueous ammonium hydroxide, aqueous ammonium chloride or ammonium sulphate wash to the composition, either in addition to or instead of other salt, base or acid washes. A third aspect of the invention provides a method for manufacturing a composition for removal of a target substance from a fluid stream, the method comprising:

providing a support material;
linking this support material covalently to a target-substance-sorbent molecule that comprises:
  a. a polyamine group; and
  b. a covalently linked hydrophobic group.

It will be appreciated that the above statements are to be read in conjunction with the embodiments described in further detail below. Each embodiment of the invention may be utilised in isolation or in combination with other embodiments, unless otherwise specified.

DETAILED DESCRIPTION OF THE INVENTION

Figure 1:
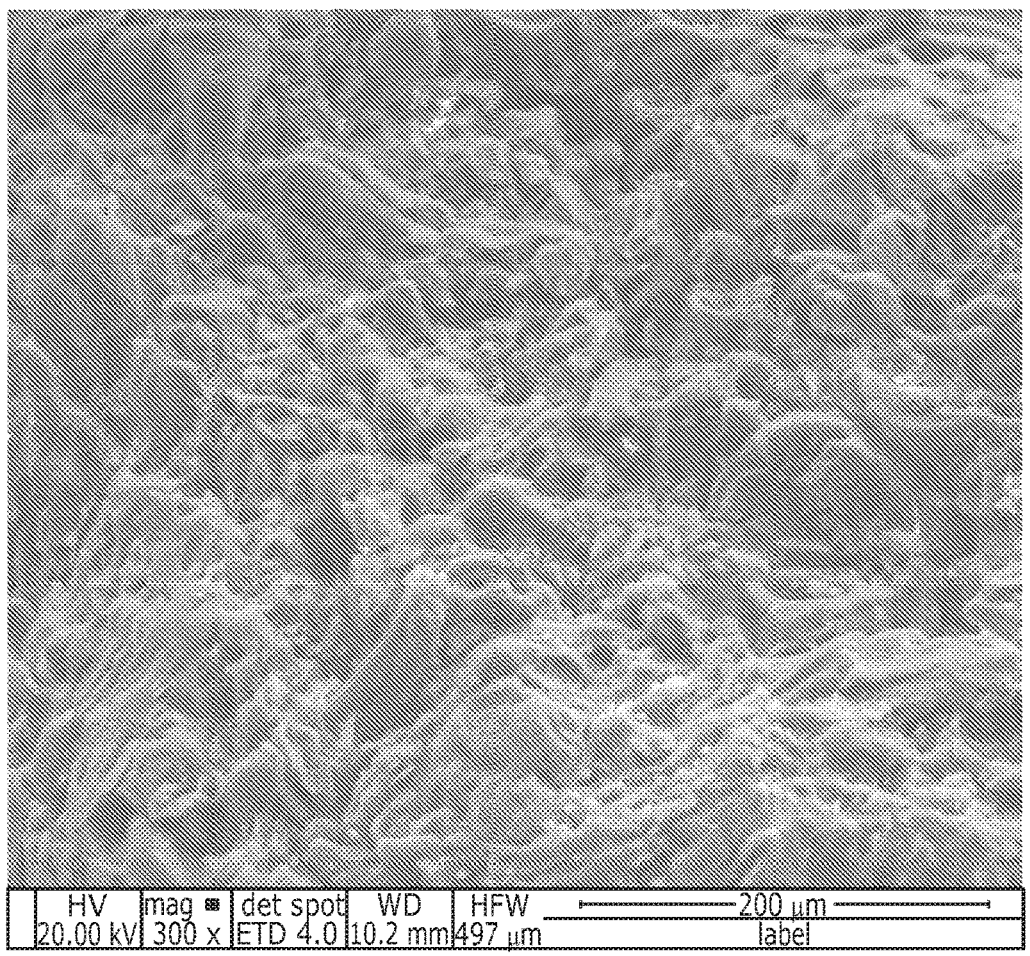
FIG. 1 shows an electron micrograph of a composition according to an embodiment of the invention.

Unless otherwise indicated, the practice of the present invention employs conventional techniques of chemistry, materials science and process engineering, which are within the capabilities of a person of ordinary skill in the art.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term 'comprising' means any of the recited elements are necessarily included and other elements may optionally be included as well. 'Consisting essentially of' means any recited elements are necessarily included, elements that would materially affect the basic and novel characteristics of the listed elements are excluded, and other elements may optionally be included. 'Consisting of' means that all elements other than those listed are excluded. Embodiments defined by each of these terms are within the scope of this invention.

The term 'target' or 'target substance' refers herein to a substance or compound which it is desired to remove or isolate from a fluid. Target substances can be dissolved (i.e. a solute), suspended, emulsified, dispersed, or otherwise carried in the fluid, and as such may be soluble, partially soluble or insoluble in the fluid. As discussed below, target substances can comprise contaminant substances and/or valuable substances which it is desired to remove, and in some cases recover, from the target fluid.

Target substances as contemplated herein can include 'contaminants' or 'contaminant substances'. In the context of the present invention, 'contaminants' are intended to encompass substances which may be harmful to the health of humans or animals, or to the environment. Consequently, derivative terms are defined accordingly, for example, a contaminated fluid is a fluid comprising a contaminant substance. Typically, the contaminant comprises one or more per- and polyfluoroalkyl substances (PFAS), typically one or more perfluorocarbons, optionally selected from a perfluorinated anionic surfactant compound, including one or more selected from the group consisting of: perfluorooctanoic acid (PFOA); perfluorobutane sulfonate (PFBS); perfluorohexanesulfonate (PFHS); perfluorohexanoic acid (PFHA); perfluorooctane sulfonate (PFOS); perfluorononanoic acid (PFNA); and perfluorodecanoic acid (PFDA) 6:2 fluorotelomer sulfonic acid (6:2 FTSA). In some embodiments, the contaminant comprises an organic compound, optionally a pharmaceutical or pesticide molecule including one or more selected from the group consisting of: diclofenac, erythromycin, estrogens, oxadiazon and thiamethoxam. The contaminant may in some embodiments be a metal or metalloid ion, optionally selected from copper, iron, lead, mercury, chromate or arsenate.

The target substance may be a valuable substance. A substance may be valuable if it contains rare elements or molecules, is a complex molecule which is difficult to manufacture, or is in any other way economically valuable enough to want to recover from a fluid. Valuable substances may be present in a fluid as a result of manufacturing, refining, mining, purification, or recovery processes. In some cases, valuable substances may also in their own right be contaminants, for example if they are harmful to the health of humans or animals, or to the environment. Valuable substances may suitably be precious metals, rare earth metals, base metals, or platinum group metals, or salts thereof. Precious metals may include gold and silver. Platinum group metals may particularly include platinum and palladium. Valuable substances may in some embodiments be small molecules, such as drugs or fine chemicals.

The term 'fluid stream' or 'fluid' refers to a flowable substance in which the target substance is dissolved, suspended, emulsified, dispersed, or otherwise carried. The fluid can be for example a liquid, or a gas. Suitably the fluid is a liquid, optionally the liquid is selected from: water; an organic solvent; a liquid fossil fuel; a liquid lubricant; an ionic liquid; a working fluid; and mixtures thereof.

The term 'cellulose' refers to a biological polymer which is a linear polysaccharide composed of glucose monomers linked with β(1→4) glycosidic bonds. Cellulose may also refer to material which further comprises hemicellulose, a polysaccharide composed of glucose and other monosaccharides, which is branched and has shorter chains than are found in cellulose.

Lignocellulose, or lignocellulosic biomass, refers to a biological material comprising cellulose and lignin, which may also comprise hemicellulose and pectin. Lignocellulose comprises much of the biomass of plants and as such is known for its high availability and resistance to degradation. This resistance is a consequence of the lignin molecules creating crosslinks between cellulose and hemicellulose chains through ester and ether linkages, Lignocellulose may be obtained from a number of sources, which include any terrestrial plant matter harvested for the purpose, or industry-related feedstocks or waste biomass produced from sources such as agriculture, forestry, construction, pulp and paper production and biofuel production. Typically, lignocellulose is obtained from agricultural wastes such as pips, husks, shells and stover (discarded leaves and stalks after the harvesting of grain). In particular, the lignocellulose can be derived from nut shells or the pips, stones, seeds or pits of fruits. The lignocellulose is dried, then crushed and sieved to the predetermined particle size.

The terms 'bacterial cellulose', 'microbial cellulose', 'nanocellulose', 'bacterially produced cellulose' and 'bacterially produced nanocellulose' as used herein are equivalent and refer to cellulose produced by bacteria or microorganisms, such as species from the genera of *Gluconacetobacter*, and others, that is characterised by high tensile strength, high tensile stiffness, high chemical purity, biocompatibility and high water-to-cellulose ratio. Suitably such bacterial nanocellulose will be substantially free of associated molecules typically present in plant-derived cellulose such as lignin. 'Microfibrillated cellulose' refers to cellulose processed by mechanical treatment with or without enzymatic or chemical pre-treatment. The material consists of long thin fibres, micrometers in length. 'Microcrystalline cellulose' refers to a pure partially depolymerized cellulose produced by breaking down amorphorous regions of the cellulose via physical, chemical or enzymatic means to leave crystalline domains.

The term 'modified' as used herein in the terms 'modified cellulose' or 'modified lignocellulose' refers to cellulose or lignocellulose which has been modified by the addition of chemical compounds. These compounds may be linked to the cellulose or lignocellulose by covalent bonds, ionic bonds, electrostatic bonds or affinity interactions. Modification may include where a chemical compound linked to the cellulose or lignocellulose is subsequently itself modified by reaction with another compound, and so forth. In particular, it is envisaged that cellulose may be modified by the addition of target substance sorbent molecules. Other possibilities for modification include the addition of polyamine groups, typically polyethylenimine. The polyamine groups may be linear or branched and are suitably branched polyethylenimine. The polyamine groups may themselves be further modified by the addition of further chemical groups, such as hydrocarbon groups.

The term 'silica' refers to materials comprising of silicon dioxide, with the formula SiO2. These may or may not be hydrated and may in a granular, porous form referred to as 'silica gel'. Alternatively, the silica-based material may be a silicate mineral such as sodium silicate.

The term 'sorbent material' as defined herein refers to a material comprising a support material, which further comprises a sorbent functional group. The sorbent material is suitable for contacting a fluid stream that comprises a target substance, such as a contaminant, which may be a PFAS, such that the target substance is adsorbed onto, absorbed into, or otherwise taken up by the sorbent material. Suitably the sorbent material is deployed within a bed or a packed column and the fluid stream is passed through or across the bed or packed-column. The sorbent material may be deployed within a mixed bed combined with another adsorbent material such as granular activated carbon or an ion-exchange resin. In one embodiment the sorbent material is comprised within a prepared component such as a cartridge, so that used sorbent material can be conveniently contained, and similarly replaced or replenished with fresh or regenerated sorbent material as necessary. Alternatively, the sorbent material may be added to the fluid as a dispersion. The sorbent material may be particulate, that is to say in the form of granules; flakes; beads; pellets; or pastilles. The sorbent material may be a powder or a pulp, in particular a cellulose, microfibrillated cellulose, microcrystalline cellulose, or lignocellulose powder or pulp which can advantageously provide higher accessible surface area. The sorbent material may be incorporated into a membrane, or membrane-like filter. In particular, a pulp can be used to make membranes or membrane-like products, which can be used to make filters. An advantage of filters of this kind is that they can be made with specific thickness, and with a large surface area, while also ensuring that fluid passes through when appropriately installed in a fluid flow path. Typically, the sorbent material is particulate or granular in form, suitably the average diameter size of the particles or granules (as measured by the largest diameter of the particles) is greater than about 0.01 mm, suitably greater than about 0.1 mm, and typically less than about 1 mm, and optionally less than about 500 µm.

The term 'sorption', 'sorb', 'sorbent' and derivatives as used herein refer to the removal of target substances such as contaminants from the fluid stream by the association of said target substances with the modified support material described. Sorption by the material may happen by any means, for example by adsorption to the surface of the material, which may be by the creation of chemical bonds between the target substance and the support material, including electrostatic attraction, the formation of covalent bonds, ligation, chelation, van der Waals forces, hydrogen bonds, or otherwise. 'Sorption' also refers to absorption of the target substance into the material. The target substance may become physically trapped inside intermolecular space, pores or other voids within the material. In particular, sorption may be adsorption occurring by the formation of chemical interactions between the target substance molecule and the sorbent molecule with which the sorbent material has been modified. Such chemical interactions lead to the sequestration of the target substance within the sorbent material and out of the fluid stream. Use herein of the term 'adsorption' or derivatives thereof is not intended to be bound by any theoretical limitation, but rather is intended to include sorption by other means, as defined above, except where otherwise specified.

In one embodiment of the present invention there is provided a composition for removal of target substances and/or contaminants from a fluid stream. The composition comprises a sorbent material comprising a support material covalently linked to a target substance sorbent molecule. The support materials have high surface area to volume ratio and therefore provide an efficient support for molecules which are able to act as sorbents for target substances. The granular sorbent particles are designed to be deployed as a sorbent media for wastewater treatment in a standard packed bed. The granules have some porosity but are hard, durable and resistant to degradation.

Where the sorbent material comprises cellulose, the particles may be produced from agricultural waste such as stover, pips and shells, and processed into granular particles by crushing and sieving. After chemical modification with target substance sorbent molecules as discussed below, the sorbent granules can be deployed in a standard packed filtration bed or column, as with other media deployed in this way (granular activated carbon or ion-exchange resins). They may be positioned such that they are contacted by a fluid stream such as wastewater comprising target substances. The fluid stream may flow over or through the granules by positive or negative pressure, such as implemented by a gravity feed, or pumping, vacuuming or otherwise impelling the fluid stream by any suitable means. Sorption occurs of the target substances by the granular sorbent material and the target substances therefore remain in situ whilst the water flows through and has the target substance removed. The filtration bed or column may be occasionally backflushed, to clear build-up of occlusions, such as organic matter or lime scale, that reduce flow rate.

According to an aspect of the invention, the sorbent molecule comprises a polyamine group. Polyamines are compounds comprising more than two amino groups. Typically, the sorbent molecules comprise polymers based on polyamines typically in the molecular weight range of 500 to 50,000 Daltons (Da). For example, the minimum average molecular weight of the polymers may typically be at least 500, at least 1000, at least 2000, at least 3000, at least 5000, suitably at least 10,000 Da. The maximum average molecular weight of the polymers may suitably be at most 50,000, at most 45,000, at most 40,000, at most 35,000, typically at most 30,000 Da. These polymers may be linear or branched. Highly branched polyamine polymers, typically termed 'dendrimers', comprise a plurality of primary amino groups on each polymer molecule. It is advantageous, in certain embodiments, if the polyamines utilised in the sorbent molecules of the invention comprise at least one terminal amine, typically the dendrimeric polyamines will comprise a plurality of terminal amines. Suitably, the sorbent molecule comprises polyethylenimine 'PEI' (also known as polyaziridine) which is a polymer composed of multiple amine groups, each linked with a saturated two carbon spacer. Typically the polyethylenimine molecules are branched, that is, they contain tertiary amine groups at branch points and primary amine groups at the terminus of each branch. Branched polyamines have lower melting points and higher solubilities, which offer advantages in production processes. In the sorbent compositions they may have steric advantages with the amines spatially arranged to allow cooperative interactions with the target molecules. In further embodiments the polyamine may comprises a linear or branched polypropyleneimine (PPI). In yet further embodiments of the invention the polyamine may comprises a linear polyamine such as, but not limited to, poly(allylamine), poly(vinylamine), poly(N-methylvinylamine)polylysine, and poly(4-aminostyrene). In an alternative embodiment of the invention, the polyamine is selected from a cationic polyamine such as Poly(diallyldimethylammonium chloride), a guanidine polyamine such as polyhexamethylene guanidine or polyhexanide, a polyamine copolymer such as poly(acrylamide-co-diallyldimethylammonium chloride).

Polyamines and modified polyamines on solid supports have previously been used as sorbent materials for gases, particularly carbon dioxide (see for example WO2015084521A1).

In water treatment, polyamines bound to solid support materials have been shown to be effective at removing heavy metals and dyes (see for example CN103041780B). However, their effectiveness at removing anionic surfactants from water is surprising. In particular, sorbent granules modified with flexible branched polyamines according to an embodiment of the invention can remove PFAS from wastewater down to regulatory limits with faster, more efficient sorption than activated carbon and lower cost than speciality ion-exchange resins. In addition, unlike with activated carbon and resins, the sorbent material can then be regenerated with an aqueous liquid wash, to recover the pollutants and reuse the sorbent material. Flexible, branched polyamines allow stronger, more specific interactions with these target pollutants. In addition, branched polyamines provide multiple amine groups where subsequent chemical substitution is possible, allowing a high degree of substitution, without the necessity for a high level of chemical modification of the cellulose itself. This tends to increase the capacity for sorption of target substances.

Before the addition of target substance sorbent molecules, it may be necessary or desired to activate the support substrate. This activation comprises the addition of a functional group to the cellulose or silica surface. In subsequent reactions, the target substance-sorbent molecule then forms a bond with the functional group added during activation, and so is linked to the support material. The covalent linkage may be via an ester, an ether, a carbamate, or a thiocarbamate linkage. In some embodiments, a cellulose support is activated by reaction with halogenated acyl halides, typically bromoacetyl bromide. Chemically related groups with different chain lengths (methyl, propyl, butyl, pentyl, and so on) are also considered for use in this activation. In other embodiments the cellulose is activated by reaction with carbonyldiimidazole, or a cross-linking agent such as glutaraldehyde or epichlorohydrin. These activating functional groups provide chemical attachment points for the target substance-binding molecules with which the cellulose is eventually modified. These attachment points can result in a short linker existing between the support and the target substance-binding molecules. This linker may be, for example, that left by acylation with the halogenated acyl halides mentioned above (—C(=O)—C—).

In another embodiment, a granular, porous, silica gel substrate is activated by reaction with (3-Chloropropyl) trichlorosilane. This provides the chemical attachment point for formation of a covalent bond to the selected polyamine in a subsequent step.

According to the invention, the sorbent molecule comprises a polyamine group that is itself modified by the addition of a further chemical group that is suitably a short chain hydrophobic group. Typically this further chemical group is added by reaction of an alkyl or aryl acid halide or anhydride with an amine group of the polyamine group to form an amide bond between the polyamine and the hydrophobic group. Optionally the reaction is between the hydrophobic group and a terminal primary amine group comprised within the polyamine molecule. In embodiments of the invention, a plurality of hydrophobic groups are reacted with a plurality of amine groups within the polyamine molecule. In some embodiments, substantially all the terminal primary amine groups present within the polyamine molecules are reacted with a hydrophobic group.

The resultant sorbent molecule will possess unique properties of sorbency that may be tuned to the specific requirements of the sorbent material. Hence, it is an advantage of the present invention that the sorbent material may be readily optimised to target specific substances and/or contaminants within a fluid stream by modifying the chemistry of the sorbent molecule.

The primary targets for treatment in wastewater are poly or perfluorinated surfactants such as PFOA, PFOS, PFHA, PFHS, PFBA, PFBS and 6:2 FTSA.

It is also envisioned that treatment of wastewater to remove other target substances, contaminants or valuable substances (including precious or rare earth metals, for example present in wastewater from mining, purification or manufacturing processes), or treatment of other fluids such as organic solvents and oils or removal of impurities from liquid product streams, is possible. In addition, sorbent material according to the present invention could be used as a sorbent to remove target substances from gases.

Unlike other sorbents deployed in this way for organic pollutants, the granular sorbent material can be effectively regenerated in situ with an aqueous liquid wash. The liquid wash can comprise a salt wash, an acid wash, a basic wash, or a combination, such as a salt and acid wash. Suitably, the wash can comprise a liquid having a pH greater than 9, or alternatively a pH of less than 5. Optionally the wash solution comprises an aqueous ammonium hydroxide, ammonium chloride or ammonium sulphate solution. The possibility of regeneration is particularly advantageous, in that it allows for the removal of target substances for recycling, recovery or safe disposal, as well as allowing the reuse of the sorbent material. In this way the proposed method for removing target substances is further reduced in cost, and in production of waste in the form of spent sorbent material.

The regeneration process suitably includes removing the sorbent material from the fluid stream and contacting it with an aqueous solution of an acid, base and/or a salt. The acid is suitably selected from an inorganic acid including hydrochloric acid, sulphuric acid, nitric acid, phosphoric acid or alternatively an organic acid suitably selected from ethanedioic acid, hexanoic acid, ethanedioic acid or citric acid. The salt is suitably selected from a sodium, potassium or magnesium salt with a chloride, sulphate or phosphate counter ion. In some embodiments, the wash liquid has a pH less than 5, suitably less than 4, less than 3, or less than 2.

Suitably, the regeneration process can instead comprise contacting the sorbent material with a basic solution, typically aqueous ammonium hydroxide. Other suitable alkali solutions may be selected from sodium or potassium hydroxides. In some embodiments, the wash liquid has a pH greater than 8, suitably greater than 9, or greater than 10.

Without wishing to be bound by theory, the adsorption of target substances to compositions as described herein appears to be the result, primarily, of electrostatic interactions with the polyamine combined with hydrophobic-hydrophobic interactions with the covalently linked hydrophobic group. In the regenerating aqueous wash solution, interactions with anions in the wash such as chloride, sulphate or hydroxide substitute for the electrostatic interactions with anionic target substances, releasing the target substances in the wash. Raising or lowering the pH changes the protonation of the polyamine, which may further reduce the electrostatic binding interactions with the adsorbed target compounds. The presence of other ions such as ammonium, can improve the solubility of adsorbed target compounds, further increasing their removal in the regenerating aqueous wash.

Another salient advantage of the present system is its low cost and ease of production. Production of granules or other forms of sorbent material such as a pulp, with a relatively low-cost polyamine (PEI) and very low-cost support material (lignocellulose) allows cost effective production of the material at large scale (~1000 kg per batch) allowing deployment in large volume wastewater applications (megalitres/day flow rate). In addition, the reactions involved with linking the cellulose substrate with the target substance-sorbent molecules may be carried out in large scale and, economically, at room temperature and atmospheric pressure.

According to a specific embodiment of the present invention, there is provided a process for the preparation of a lignocellulose ester that is then modified with amphipathic groups in order to generate a derivative product with particular utility in filtration and removal of PFAS from liquid streams. A particular advantage of the product of this embodiment of the present invention is that the process does not require elevated temperatures as it can take place at room temperature, nor does the reaction require expensive catalysts, especially metal containing catalysts. Hence, the process for preparation of the product is relatively energy efficient and less resource intensive, thereby adding to the improved economics of production. Further, the process shows additional advantage in that the resultant product can be regenerated after use, reducing the overall consumption of the product and enhancing the effective working life beyond that of comparable sorbents, as well as allowing for the recovery of any valuable substances removed from the treated fluid stream.

In an embodiment of the present invention the lignocellulose/cellulose support material is activated by esterification with bromoacetyl bromide at room temperature in the presence of dimethyl formamide (DMF) according to the following reaction scheme I:

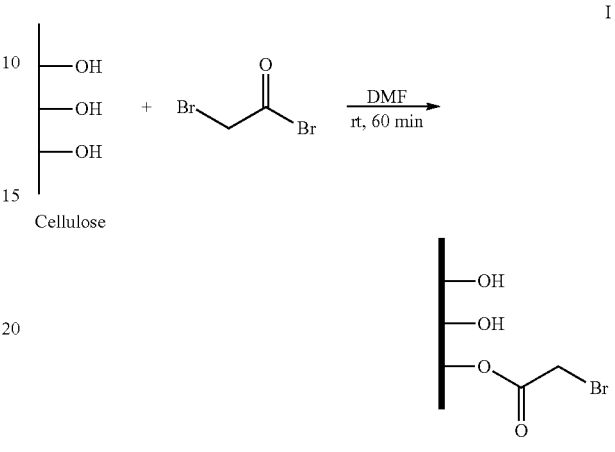

It will be appreciated that in alternative embodiments a different reactant may be used to esterify the cellulose in a similar reaction, such as other halogenated acyl halides, suitably chloroacetyl chloride, chloroacetyl bromide, and bromoacetyl chloride; or halogen propionyl or butyryl halide.

The bromoacetylated form of the lignocellulose is further reacted with a polyamine also in the presence of DMF at room temperature in order to achieve a highly substituted lignocellulose derivative. In the present embodiment of the invention, the amine utilised in the second step of the reaction is a branched polyethyleneimine (PEI) according to the following reaction scheme II:

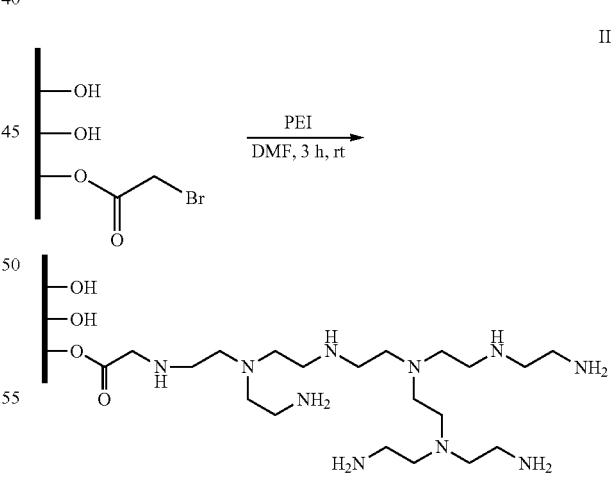

It will be appreciated that straight chain (linear) PEI may also be used, as well as other polyamines, such as polypropyleneimine (PPI), poly(allylamine), poly(vinylamine), poly(N-methylvinylamine), polylysine, poly(4-aminostyrene), poly(diallyldimethylammonium chloride), polyhexamethylene guanidine, polyhexanide, poly(methylene co-guanidine), or poly(acrylamide-co-diallyldimethylammonium chloride).

In another embodiment the particulate, support material is a silica gel. In this embodiment, the silica surface is hydrated then activated by reaction with Trichloro(3-chloropropyl) silane in hexane solvent. The product is dried, and then the polyamine is covalently bound, by reacting in a methanol solvent according to the following reaction scheme III.

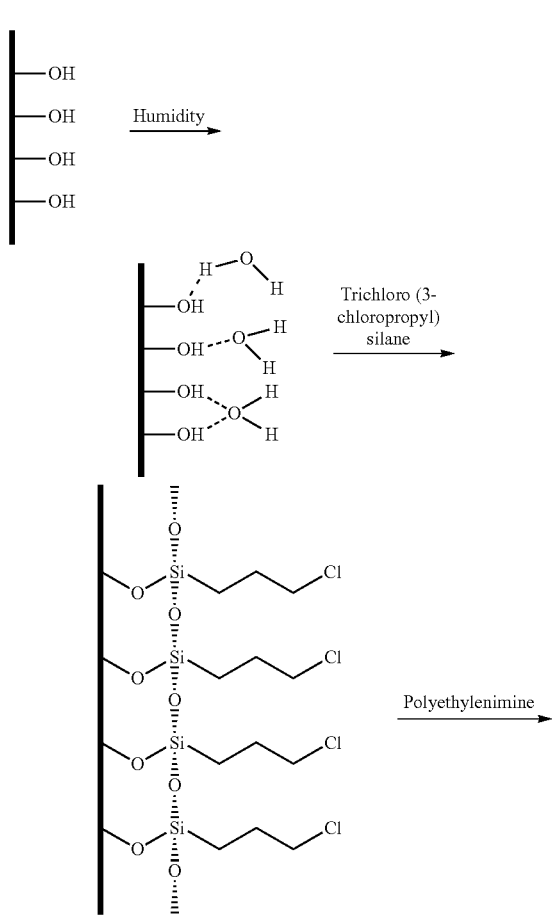

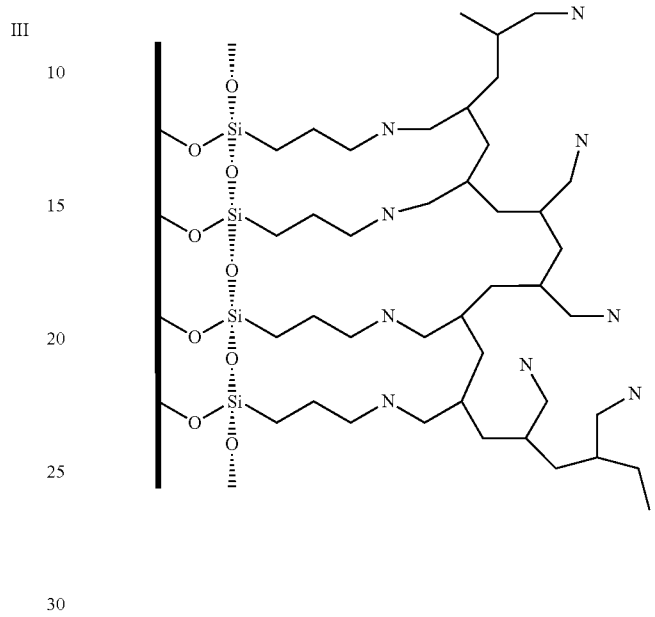

The substituted, particulate solid support product is further reacted in a third step with, for example, an acylating agent, suitably an acyl or aryl acid halide. In the present embodiment of the invention, hexanoyl choride is used in the acyl substitution of primary amines within the PEI group bonded to the solid support. The hexanoyl chloride is dissolved in dichoromethane (DCM) and the reaction is carried out also at room temperature in the presence of the base and catalyst diisopropylethylamine (DIPEA), as set out in the following reaction scheme IV, the hydrophobic group is linked to the polyamine via an amide bond:

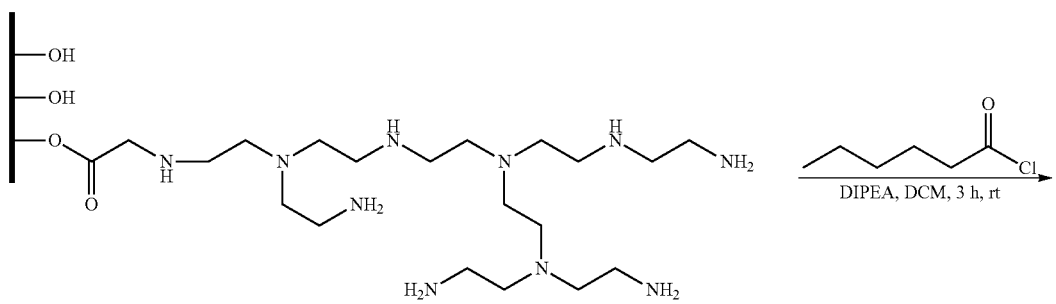

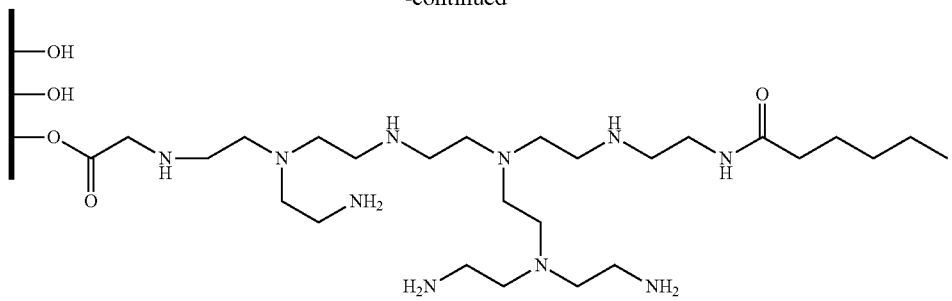

It will be appreciated that in alternative embodiments of the invention the acylating agent may comprise a compound of the formula:

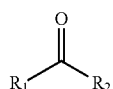

Wherein:

$R_1$ is a C2-C22 branched, linear or cyclic alkyl; or an aryl group $R_2$ is a halide.

Typically $R_1$ is selected from a C2-C22, suitably a C4-C8, linear saturated or unsaturated alkyl group, most suitably selected from a butyl, hexyl or octyl group. Optionally $R_1$ is selected from an isopropyl, isobutyl or isohexyl group. $R_1$ may comprise a cycloalkyl selected from a cyclobutyl or cyclohexyl group. Where $R_1$ is an aryl, typically the aryl is selected from a phenol or benzyl group.

$R_2$ is typically selected from a chloride or a bromide.

Alternatively the polyamine covalently bound to a granular solid support material may be modified by covalent addition of a C2-C22 hydrophobic group by one of the following reactions:

A reaction according to scheme V where the polyamine group is linked to the hydrophobic group via an urea bond. wherein $R_2R_3NH$ represents the polyamine group and $R_1$=C2 to C22. The reaction is peformed under the basic conditions in an aprotic solvent system.

V

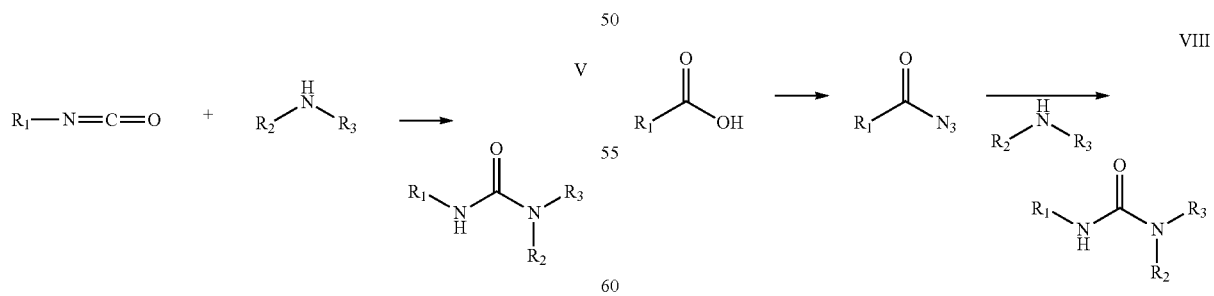

The urea unit can alternatively be formed by a reaction shown in Scheme VI, wherein $R_3R_4NH$ represents the polyamine group and $R_1$=C2 to C22 and $R_2$=H. The reaction is performed under basic conditions in an aprotic solvent system, employing a carbonyldiimidazole derivative.

VI

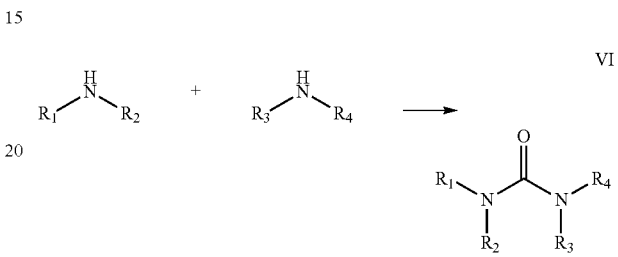

The urea unit can alternatively be formed by a reaction shown in Scheme VII, wherein $R_2R_3NH$ represents the polyamine group and $R_4$=C2 to C22 and $R_5$=H, and $R_2$=a hydrocarbon unit. The reaction is performed under basic conditions in an aprotic solvent system.

VII

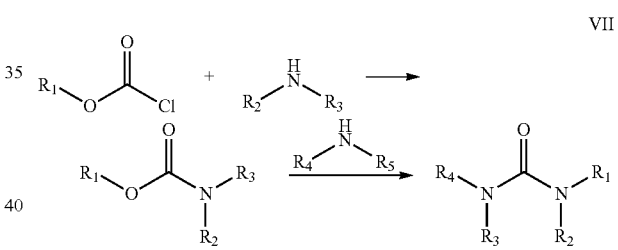

The urea unit can be formed by a reaction shown in Scheme VIII, wherein $R_2R_3NH$ represents the polyamine group and $R_1$=C2 to C22. The reaction is performed under basic conditions in an aprotic solvent system and an azide-containing reagent for step1.

VIII

Alternatively, the C2-C22 hydrophobic group may be covalently attached to the polyamine via a quaternisation (Menshutkin) reaction, resulting in nitrogens of the polyamine becoming bound to up to three C2-C22 hydrophobic groups. This may be by a reaction shown in Scheme IX, wherein X=halide, $R_4$=C2 to C22 hydrophobic group, $R_1$=part of the polyamine molecule and $R_2$ and $R_3$=$R_4$ or are part of the polyamine molecule represented by $R_1R_2R_3N$.

IX

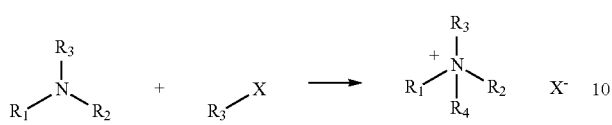

The invention is further illustrated by the following non-limiting examples:

Example 1

The novel custom granular media (CGM) compositions of the invention demonstrate significantly improved capacity for adsorption of PFAS in part due to their unique structure (see FIG. 1). This Figure shows an electron micrograph of a composition, comprising porous, solid, particulate, lignocellulose material covalently linked to polyetheleneimine (average mw, 25,000), covalently linked to a plurality of C6 hydrophobic groups via reaction with hexanoyl chloride. The composition displays surface roughness on a micrometre scale, allowing for the adsorption of larger quantities of PFAS.

Figure 2:
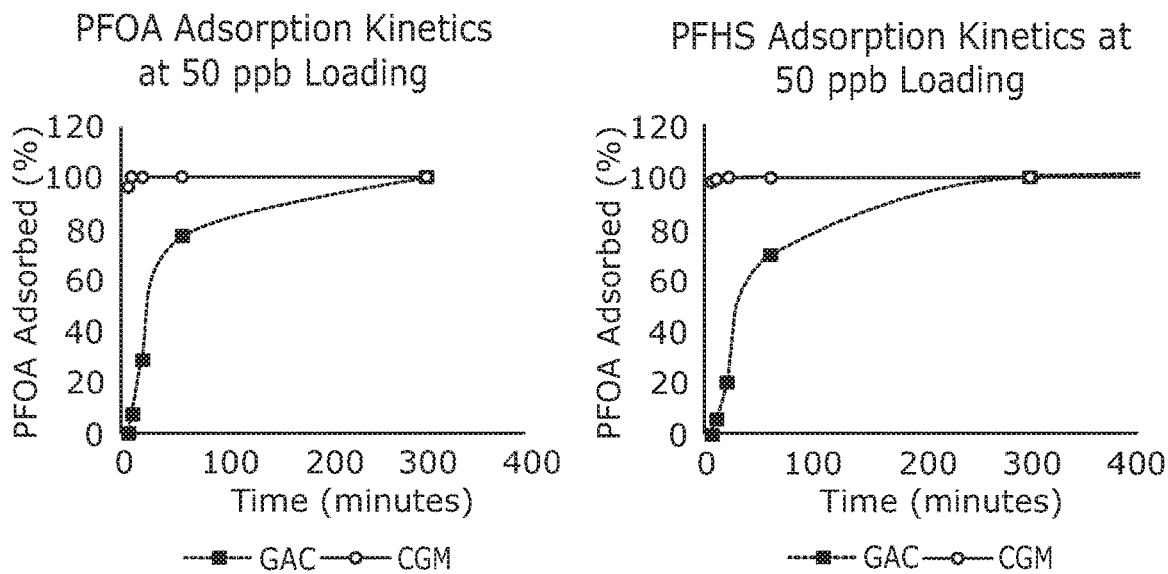
FIG. 2 shows graphs comparing adsorption kinetics of PFAS compounds between a composition according to the invention (CGM), and bituminous granular activated carbon (GAC).

The absorption kinetics of a CGM composition of the invention were compared with a conventional bituminous granular activated carbon (GAC) media. In the assay 0.05 g of each adsorbent (1 mm average diameter granules) were soaked in 40 mL of 50 ppb PFOA or PFHS in DI water. At certain time points aliquots of the solution were taken and PFAS concentrations quantified using Liquid Chromatography-Mass Spectrometry/Mass Spectrometry (LC-MS/MS). The results are shown in FIG. 2. It can be seen that CGM has much faster kinetics compared to GAC for both PFOA and PFHS adsorption. In practice, the far superior kinetics seen for CGM translates to significantly reduced contact time for treatment allowing faster fluid flow rates or use of smaller vessels. Furthermore, the improved kinetics allow for flexible hydraulic loading requirements to fit with any required pre- or post-treatment.

Example 2

Figure 3:
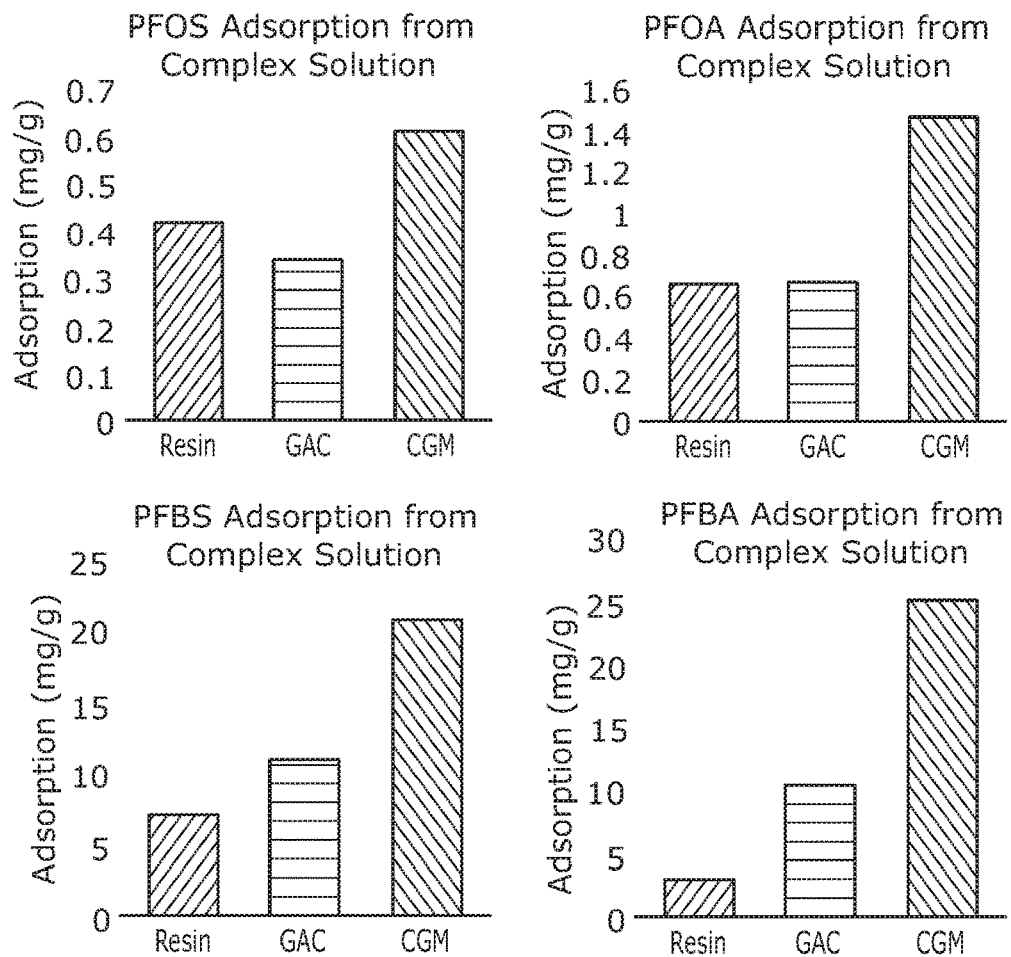
FIG. 3 demonstrates improved binding capacity for PFAS compounds in simulated wastewater with competing organic acids shown by a composition according to the invention (CGM), compared to a bituminous granular activated carbon (GAC) and an amberlite anion exchange resin.

The binding capacity for PFAS of the CGM composition of the invention was tested in a simulated waste water comparison to GAC and an Amberlite® anion exchange resin. Batch tests were performed in which 0.05 g of adsorbent granules were soaked in 40 mL of 2.5 ppm PFOS, PFOA, PFBS and PFBA in DI water containing 250 ppm competing organic acids. After 24 hours, the PFAS concentration in each of the solutions was quantified using LC-MS/MS as in Example 1. The results of the tests are set out in FIG. 3. In all instances CGM, the composition of the invention, outperformed the conventional sorbent media.

Example 3

Figure 4:
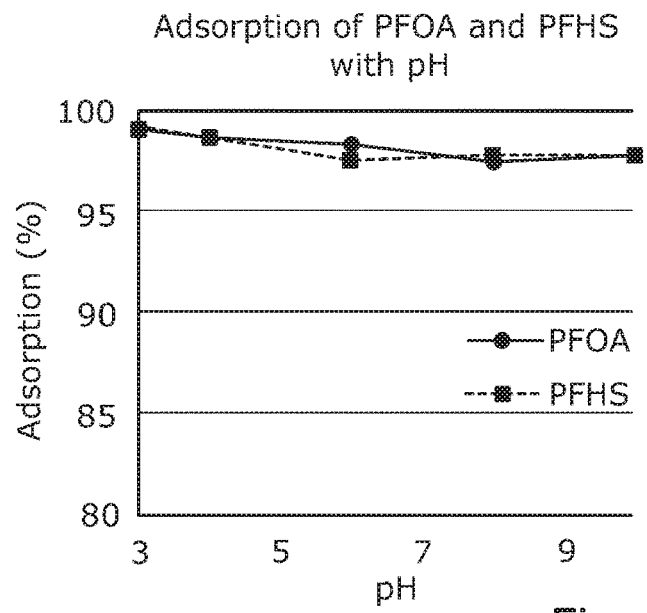
FIG. 4 shows performance of a composition according to the invention at adsorbing PFOA and PFHS from batch tests at a range of pH values.

The CGM composition of the invention was tested for adsorption performance across a pH range from acidic to basic conditions, as might be encountered in waste effluent from industrial or agricultural sources. According to this assay 0.05 g of adsorbent granules were soaked in 40 mL of 2.5 ppm, PFOA or PFHS solution in DI water, pH adjusted with NaOH or HCl accordingly. After 24 hours, the PFAS concentration in the solutions was quantified using LC-MS/MS as per Example 1. The results are shown in FIG. 4. As can be seen, high levels (>97%) of PFAS adsorption are observed and remain surprisingly stable across all of the pH ranges tested.

Example 4

Figure 5:
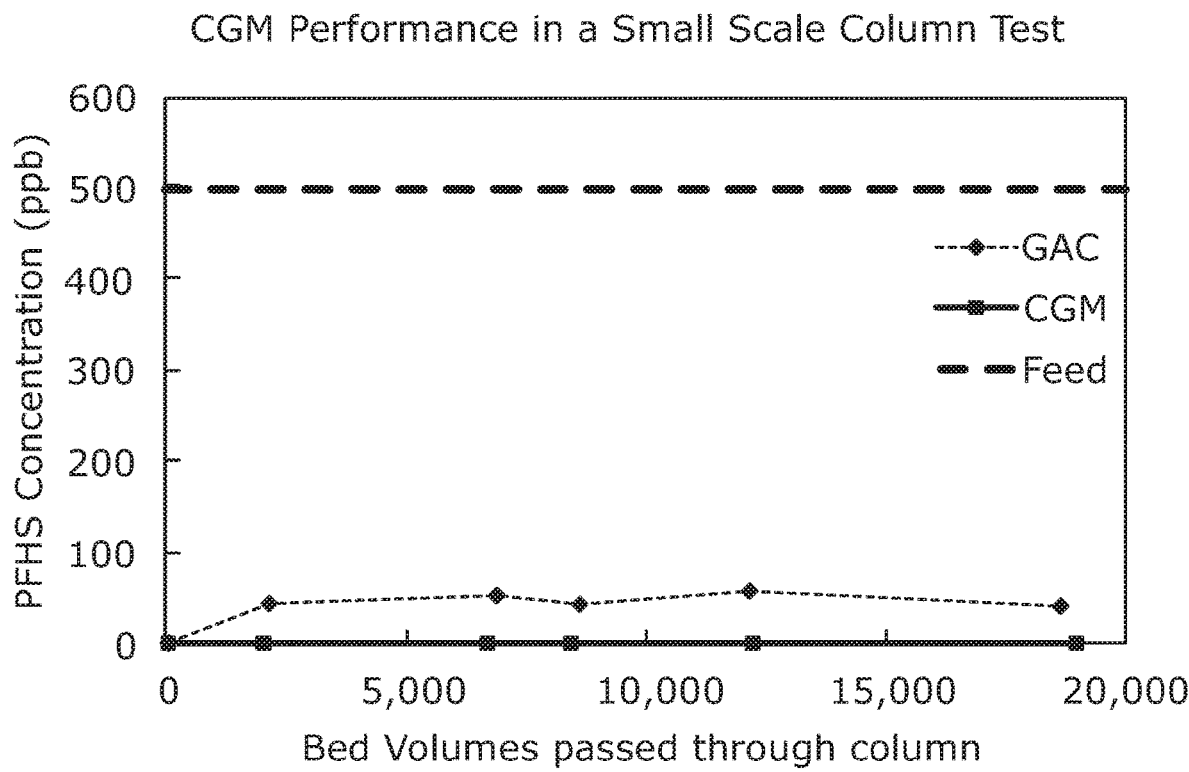
FIG. 5 shows performance of a composition according to the invention (CGM) in a rapid small-scale column test for the removal of the contaminant PFHS over a range of bed volumes passed through the column.

The CGM composition of the invention was tested in a rapid small-scale column test for removal of the contaminant PFHS. The contaminated water influent (feed) contained PFHS at 500 ppb and was pumped through small packed beds of the CGM composition and a competitor granular activated carbon (GAC). The contact time was 22 seconds, with 7.5 m/h linear velocity. Samples of the effluent solution were taken and PFHS quantified by LC-MS/MS. Results are shown in FIG. 5. The CGM composition showed removal of the target contaminant to non-detectable levels over 20,000 bed volumes (BV) of influent solution being treated. This was not achieved by GAC, where the conventional sorbent media showed an effluent concentration which quickly rose to approximately 50 ppb.

Example 5

Figure 6:
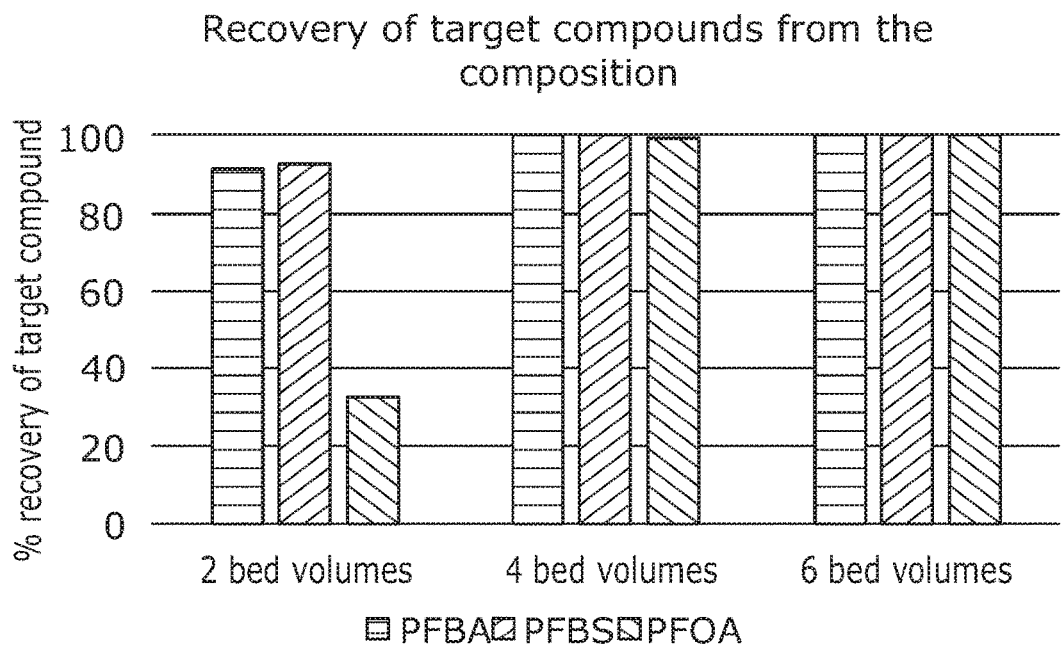
FIG. 6 shows the percentage recovery of target compounds, PFBA, PFBS and PFOA, from a composition according to the invention using a regeneration solution of 3% aqueous ammonium hydroxide over a range of bed volumes passed through the column.

The CGM composition of the invention was mixed with a contaminated solution containing PFOA, PFBA and PFBS in a batch test. The CGM composition adsorbed 50 µg of total contaminant substance per gram of material (50 µg/g loading). The loaded CGM media was then packed into an 8 ml packed bed. A regeneration solution of 3% aqueous ammonium hydroxide was pumped through, with a contact time of 15 minutes. The total regeneration solution passed through the column was collected and sampled after every 2 bed volumes (8 ml). PFOA, PFBA and PFBS concentrations were quantified by LC-MS/MS and total recovery of the compounds was calculated based on the initial loading amount. Results are shown in FIG. 6. The shorter chain PFBA and PFBS are quickly recovered and after 6 bed volumes of regenerant solution, all of the target substances have been recovered from the sorbent composition, and are present in the spent regenerant solution.

The invention claimed is:

1. A composition for removal of a target substance from a fluid stream, the composition comprising:
   a) a sorbent molecule comprising:
      i) a branched polyamine, and
      ii) a hydrophobic group covalently linked to the branched polyamine; and
   b) a cellulose-containing support material covalently linked to the branched polyamine.

2. The composition of claim 1, wherein the cellulose-containing support material is comprised of a material selected from one or more of the group consisting of: lignocellulose; bacterial cellulose; microcrystalline cellulose; microfibrillated cellulose and a cellulose derivative.

3. The composition of claim 2, wherein the cellulose-containing support material comprises a cellulose or lignocellulose powder or pulp.

4. The composition of claim 1, wherein the cellulose-containing support material is porous, solid, and particulate.

5. The composition of claim 1, wherein the branched polyamine is selected from the group consisting of:

polyethylenimine (PEI); polypropylenimine (PPI); poly (allylamine); poly(vinylamine);
poly(N-methylvinylamine); polylysine; poly(4-aminostyrene);
poly(diallyldimethylammonium chloride); polyhexamethylene guanidine; polyhexanide;
poly(methylene co-guanidine); and poly(acrylamide-co-diallyldimethylammonium chloride).

6. The composition of claim 1, wherein the hydrophobic group comprises a C2-C22 alkyl group.

7. The composition of claim 1, wherein the hydrophobic group comprises a polyfluoroalkyl group or perfluoroalkyl group.

8. The composition of claim 1, wherein the sorbent molecule comprises a plurality of hydrophobic groups.

9. The composition of claim 1, wherein the branched polyamine is linked to the hydrophobic group via a bond selected from the group consisting of:
an amide bond; a urea linkage; a thiourea linkage; an isothiouronium linkage; a guanidinium linkage; and a quaternisation (Menshutkin) reaction.

10. A process for removal of a target substance from a fluid stream comprising contacting the fluid stream with a composition of claim 1.

11. The process of claim 10, wherein the fluid is a liquid.

12. The process of claim 11, wherein the liquid is selected from:
an organic solvent; a liquid fossil fuel; a liquid lubricant; an ionic liquid; and a working fluid wherein the working fluid comprises water.

13. The process of claim 10, wherein the target substance comprises one or more poly- and perfluorinated alkyl substance (PFAS).

14. The process of claim 13, wherein the PFAS is a perfluorinated anionic surfactant compound.

15. The process of claim 14, wherein the perfluorinated anionic surfactant compound is selected from the group consisting of:
perfluorobutane sulfonate (PFBS); perfluorobutanoic acid (PFBA);
perfluorohexanesulfonate (PFHS); perfluorohexanoic acid (PFHA); perfluorooctanoic acid (PFOA); perfluorooctane sulfonate (PFOS); perfluorononanoic acid (PFNA); and
perfluorodecanoic acid (PFDA); and 6:2 fluorotelomer sulfonic acid (6:2 FTSA).

16. The process of claim 10, wherein the cellulose-containing support material is cellulose or lignocellulose powder or pulp incorporated into a membrane or membrane-like filter.

17. The process of claim 10, wherein the cellulose-containing support material is porous, solid, and particulate and is in the form of one or more of: granules; flakes; beads: pellets; and pastilles.

18. The process of claim 10, wherein the cellulose-containing support material is comprised within a bed or a packed column and the fluid stream is passed through or across the bed or packed column.

19. The process of claim 10, wherein the process further comprises regenerating the composition after removal of the target substance from the fluid stream.

20. The process of claim 19, wherein regenerating the composition comprises applying one or more aqueous liquid washes to the composition, and wherein one or more of the liquid washes is a salt wash.

21. The process of claim 19, wherein regenerating the composition comprises applying one or more aqueous liquid washes to the composition, and wherein one or more of the liquid washes is an acid wash.

22. The process of claim 19, wherein regenerating the composition comprises applying one or more aqueous liquid washes to the composition, and wherein one or more of the liquid washes is a basic wash.

23. The composition of claim 1, wherein the hydrophobic group comprises an alkyl group selected from the group consisting of:
a butyl group; a hexyl group; and an octyl group.

24. The composition of claim 1, wherein the hydrophobic group comprises an alkyl group selected from the group consisting of:
an isobutyl group; an isohexyl group; and an isooctyl group.

25. A composition suitable for the removal of one or more poly- and perfluorinated alkyl substance (PFAS) from water, the composition comprising:
a) a branched polyamine, wherein the branched polyamine is polyethylenimine (PEI);
b) a hydrophobic group comprising a hexyl group and covalently linked to the branched polyamine via an amide bond; and
c) a cellulose-containing support material covalently linked to the branched polyamine.

* * * * *